United States Patent [19]

Ash et al.

[11] 4,423,222

[45] Dec. 27, 1983

[54] PYRIDINYL FUNGICIDES AND HERBICIDES

[75] Inventors: Mary L. Ash; Richard G. Pews, both of Midland, Mich.

[73] Assignee: The Dow Chemical Company, Midland, Mich.

[21] Appl. No.: 380,644

[22] Filed: May 21, 1982

[51] Int. Cl.$^3$ .................. C07D 213/61; C07D 213/40
[52] U.S. Cl. ..................................... 546/337; 546/342
[58] Field of Search ................................. 546/337, 342

[56] References Cited

U.S. PATENT DOCUMENTS

| | | | |
|---|---|---|---|
| 3,438,993 | 4/1969 | Wilbert et al. | 546/342 |
| 3,981,903 | 9/1976 | Hirano et al. | 424/305 |
| 4,163,787 | 8/1979 | Malhotra et al. | 424/263 |
| 4,175,947 | 11/1979 | Koch et al. | 546/342 |
| 4,357,336 | 11/1982 | Wong | 424/263 |
| 4,358,606 | 11/1982 | Lee et al. | 546/337 |

FOREIGN PATENT DOCUMENTS 2461458  2/1981  France .

Primary Examiner—Norma S. Milestone
Attorney, Agent, or Firm—Edward P. Gray; Ronald G. Brookens

[57] ABSTRACT

Suitably substituted 2-aminomethyl pyridines and suitably substituted 2-pyridinylcarbinols are reacted with 3-(2,2-dichloroethenyl)-2,2-dimethylcyclopropane carboxoyl chloride in an inert solvent to form a group of biologically active organic compounds. These compounds are active as fungicides, herbicides, or both.

2 Claims, No Drawings

PYRIDINYL FUNGICIDES AND HERBICIDES

BACKGROUND OF THE INVENTION

The present invention discloses novel pyridine compounds and their method of preparation. These compounds may be used as fungicides, herbicides or both.

SUMMARY OF THE INVENTION

The present invention is directed to a group of novel, biologically active compounds represented by the formula:

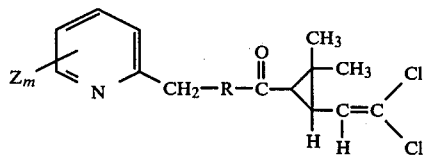

wherein R is oxygen or imino (—NH—); each Z is independently selected from the group consisting of chlorine, bromine, fluorine, and iodine; and m is an integer of from zero to four, both inclusive.

Of the compounds of the present invention, those preferred for herbicidal and/or fungicidal use are compounds wherein R is oxygen or imino, and m is zero (i.e., where the pyridine ring is not halo-substituted).

The compounds of the present invention are biologically active and effective as fungicides, herbicides or both. Typically, the compounds are effective against the causative organisms of fungal diseases such as barley powdery mildew, apple scab, wheat leaf rust and the like. As herbicides, these compounds are typically effective against a variety of grasses and plants such as barnyard grass, wild oats, velvet weed and yellow foxtail.

The compounds of the invention may be prepared by the reaction of 3-(2,2-dichloroethenyl)-2,2-dimethylcyclopropane carboxoyl chloride with a suitably substituted 2-aminomethyl pyridine represented by the formula:

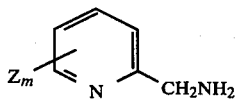

wherein Z and m have the meaning previously given; or with a suitably substituted 2-pyridinylcarbinol represented by the formula:

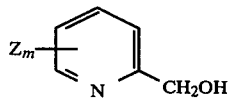

wherein Z and m have the meaning previously given.

The preparation of the substituted pyridines used as starting material for this invention are commercially available or may be readily prepared utilizing known procedures by one skilled in the art. The preparation of the ethyl 3-(2,2-dichloroethenyl)-2,2-dimethylcyclopropane carboxylate ester necessary for the production of the corresponding carboxoyl chloride is similarly known in the art. See, for example, U.S. Pat. Nos. 3,981,903 and 4,163,787 which are incorporated herein by reference. The preparation of 3-(2,2-dichloroethenyl)-2,2-dimethylcyclopropane carboxoyl chloride is set out in detail in Example I, below.

In the preparation of the compounds of this invention, the reactants are contacted in an inert solvent such as acetone or methylene chloride. While the exact proportion of the reactants employed is not critical, the reaction consumes the reactants in amounts representing essentially equimolar proportions and the use of such amounts is preferred. The mixture is heated at reflux temperature for a period of time sufficient to obtain a satisfactory yield of the desired product (usually about one to about twenty hours depending on reaction conditions). Following reaction, the solvent is removed by conventional techniques leaving a residue containing the product, which may be purified by traditional methods if needed.

DESCRIPTION OF SOME PREFERRED EMBODIMENTS

The following examples are set forth as a means of illustrating the present invention. They are specific examples of preferred embodiments and are not to be construed as a limitation on the invention.

EXAMPLE I 3-(2,2-Dichloroethenyl)-2,2-dimethylcyclopropane carboxoyl chloride Ethyl 3-(2,2-dichloroethenyl)-2,2-dimethylcyclopropane carboxylate ester (23.9 grams) was heated at reflux temperature in 60 milliliters (ml) of ethanol. Potassium hydroxide (7.5 grams) was added and the resulting solution was heated at reflux temperature for 30 minutes. The solution was cooled, and the ethanol was removed in vacuo leaving a residue which was subsequently dissolved in about 50 ml of water and extracted with methylene chloride. The methylene chloride layer was discarded and the aqueous layer was acidified with 6 N HCl, and again extracted with methylene chloride. The organic layer was dried over calcium sulfate and the solvent was removed in vacuo leaving a residue. The residue was determined to be the desired 3-(2,2-dichloroethenyl)-2,2-dimethylcyclopropane carboxylic acid having a melting point (mp) of 63°-64° C.

3-(2,2-Dichloroethenyl)-2,2-dimethylcyclopropane carboxylic acid (32.0 grams) was stirred in 400 ml of methylene chloride under nitrogen. To this was added N,N-dimethylformamide (12 ml) and thionyl chloride (22.6 grams). The resulting solution was heated at reflux temperature for about 1.5 hours. The solvent was then removed in vacuo leaving about 36 grams of the desired 3-(2,2-dichloroethenyl)-2,2-dimethylcyclopropane carboxoyl chloride, which was confirmed by IR and NMR spectroscopy.

EXAMPLE II 3-(2,2-Dichloroethenyl)-2,2-dimethyl-N-(2-pyridinylmethyl)cyclopropane carboxamide 3-(2,2-Dichloroethenyl)-2,2-dimethylcyclopropane carboxoyl chloride (38.0 grams, prepared by the procedure described in Example I) was stirred in 150 ml of methylene chloride. Slowly added to this was a solution of 16.2 grams of 2-aminomethyl pyridine in 10 ml of methylene chloride. The resulting slurry was heated at reflux temperature for 20 hours, after which it was added to about 250 ml of water, neutralized with sodium bicarbonate and extracted several times with methylene chloride. The combined organic extracts were washed with a saturated solution of sodium chloride and dried over calcium sulfate. The solvent was removed in vacuo leaving the desired, 3-(2,2-dichloroethenyl)-(2,2-dimethyl-N-(2-pyridinylmethyl)cyclopropane carboxamide having a melting point of 53°–57° C.

Elemental analysis calculated for $C_{14}H_{16}Cl_2N_2O$ (percent): carbon—56.20; hydrogen—5.39; nitrogen—9.36. Found: carbon—55.9; hydrogen—5.46; nitrogen—9.37.

EXAMPLE III

2-Pyridinylmethyl-3-(2,2-dichloroethenyl)-2,2-dimethylcyclopropane carboxylate ester 3-(2,2-Dichloroethenyl)-2,2-dimethylcyclopropane carboxoyl chloride (26.7 grams, prepared by the procedure described in Example I) was stirred in 125 ml of methylene chloride. Slowly added to this was 12.8 grams of 2-pyridinylcarbinol. The resulting slurry was heated at reflux temperature for about 1.5 hours and was then stirred at room temperature for about 10 hours. The solvent was removed in vacuo leaving an oil which was added to water and neutralized with sodium bicarbonate. The aqueous mixture was extracted several times with methylene chloride and the combined organic extracts were dried over calcium sulfate and the solvent was removed in vacuo. The resulting residue was recrystallized from hexane leaving the 2-pyridinylmethyl-3-(2,2-dichloroethenyl)-2,2-dimethylcyclopropane carboxylate ester, having a melting point of 58°–59° C.

Elemental analysis calculated for $C_{14}H_{15}NO_2Cl_2$ (percent): carbon—56.02; hydrogen—5.04; nitrogen—4.66. Found: carbon—55.9; hydrogen—5.06; nitrogen—4.66.

The compounds of the present invention may be used as fungicides, herbicides or both. For these uses, one or more of the compounds may be used in unmodified form, or may be formulated into fungicidal or herbicidal compositions. For instance, compounds of this invention can be dispersed on a finely divided solid and applied as a dust. The compounds may also be formulated into aqueous compositions, with or without the use of a wetting agent, and applied as a spray. Similarly, the compounds may be employed in liquid organic compositions, water-in-oil or oil-in-water emulsions or aqueous dispersions with or without the use of emulsifying, wetting or dispersing agents.

Not all compounds or the compositions containing them may be equally effective at similar concentrations or against similar plant or fungal organisms. While the exact amount of compound or composition employed is not critical, good results are obtained when the plant, organism, and/or their habitat is contacted with a herbicidally or fungicidally effective amount of one or more of the compounds or compositions containing them. The term "effective amount" refers to a fungicidal concentration of from about 25 to about 500 parts per million by weight of the ultimate composition. Similarly, a herbicidally "effective amount" refers to a concentration of from about 1,000 to about 2,000 parts per million by weight of the ultimate composition or about 2 to about 10 pounds per acre depending upon the mode of application.

In a representative operation, the fungicidal effects of compounds of the present invention were demonstrated. Host plants were inoculated with the causative organism of the fungal disease apple scab, and placed under conditions conducive to the growth of the organism. Aqueous suspensions of the test compounds were prepared at a concentration of 400 parts per million (ppm) and applied to the plants during the period of growth of the organism. The plants were later evaluated for degree of disease control. The compounds, 3-(2,2-dichloroethenyl)-2,2-dimethyl-N-(2-pyridinylmethyl)-cyclopropane carboxamide and the 2-pyridinylmethyl-3-(2,2-dichloroethenyl)-2,2-dimethylcyclopropane carboxylate ester, exhibited 95 and 83 percent control respectively of the causative organism of apple scab.

In similar operations, 3-(2,2-dichloroethenyl)-2,2-dimethyl-N-(2-pyridinylmethyl)-cyclopropane carboxamide exhibited 50 percent control of the causative organism of barley powdery mildew and 95 percent control of the causative organism of wheat leaf rust when applied to host plants in a concentration of 500 ppm. The causative organism of barley powdery mildew was also substantially controlled (95 percent control) when the 2-pyridinylmethyl-3-(2,2-dichloroethenyl)-2,2-dimethylcyclopropane carboxylate ester was applied to host plants at a concentration of 500 ppm.

In another operation, the herbicidal activity of the compounds of the present invention was demonstrated. Barnyard grass and yellow foxtail seeds were planted, and the soil was treated with various concentrations of test compounds. Approximately 2 weeks after treatment, the plants were evaluated and the compounds rated for pre-emergence activity (a rating of 100 represented total kill of the treated plants). When applied at a rate of 10 pounds per acre, the compound 3-(2,2-dichloroethenyl)-2,2-dimethyl-N-(2-pyridinylmethyl)-cyclopropane carboxamide showed 100 percent kill of barnyard grass. Similarly, when applied at the rate of 2 pounds per acre, the 2-pyridinylmethyl-3-(2,2-dichloroethenyl)-2,2-dimethylcyclopropane carboxylate ester exhibited a 100 percent control of yellow foxtail.

In a similar operation, the post-emergence activity of the 2-pyridinylmethyl-3-(2,2-dichloroethenyl)-2,2-dimethylcyclopropane carboxylate ester was tested. Various plant species were grown in six separate plots so that each plot contained all of the species. The plants were grown to a height of about four inches, and then each plot was sprayed to run-off with an aqueous composition of test compound prepared at a concentration of 4,000 ppm by weight. The plants were then placed in an environment conducive to growth and were evaluated two weeks later. Upon evaluation, it was found that the test compound (the 2-pyridinylmethyl-3-(2,2-dichloroethenyl)-2,2-dimethylcyclopropane carboxylate ester) showed 100 percent kill of wild oats and velvet weed.

What is claimed is:

1. A compound represented by the formula:

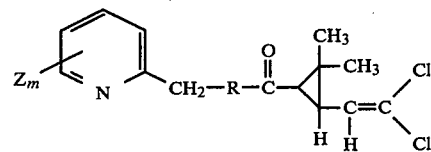

wherein, R is imino (—NH—); each Z is independently selected from the group consisting of chlorine, bromine, fluorine, and iodine; and m is an integer of from zero to four, both inclusive.

2. The compound of claim 1 which is 3-(2,2-dichloroethenyl)-2,2-dimethyl-N-(2-pyridinylmethyl)-cyclopropane carboxamide.

* * * * *